(12) United States Patent
Schirr et al.

(10) Patent No.: US 10,031,493 B2
(45) Date of Patent: Jul. 24, 2018

(54) ACTUATOR APPARATUS WITH CONTROL DEVICE

(76) Inventors: Andreas Schirr, Hamburg (DE); Andreas Graff, Hamburg (DE)

(*) Notice: Subject to any disclaimer, the term of this patent is extended or adjusted under 35 U.S.C. 154(b) by 733 days.

(21) Appl. No.: 14/127,151

(22) PCT Filed: Jun. 15, 2012

(86) PCT No.: PCT/EP2012/002536
§ 371 (c)(1),
(2), (4) Date: Mar. 13, 2014

(87) PCT Pub. No.: WO2012/171651
PCT Pub. Date: Dec. 20, 2012

(65) Prior Publication Data
US 2014/0195056 A1    Jul. 10, 2014

Related U.S. Application Data

(60) Provisional application No. 61/498,055, filed on Jun. 17, 2011.

(30) Foreign Application Priority Data

Jun. 17, 2011 (EP) .................... 11004979

(51) Int. Cl.
*G05B 15/02* (2006.01)
*C12M 1/00* (2006.01)

(52) U.S. Cl.
CPC ............. *G05B 15/02* (2013.01); *C12M 99/00* (2013.01)

(58) Field of Classification Search
CPC ................ G05B 15/02; C12M 99/00
See application file for complete search history.

(56) References Cited

U.S. PATENT DOCUMENTS 5,727,915 A * 3/1998 Suzuki ............... B25J 3/04
414/1
6,366,868 B2 * 4/2002 Freudenberg ....... F02D 41/2096
307/113

(Continued)

FOREIGN PATENT DOCUMENTS

EP     1505288 A2    2/2005
EP     1947675 A1    7/2008

(Continued)

OTHER PUBLICATIONS

Michael A. Lombardi, Fundamentals of Time and Frequency, National Institute of Standards and Technology, 2002, 18 pages.*

(Continued)

*Primary Examiner* — Thomas C Lee
*Assistant Examiner* — Tri T Nguyen
(74) *Attorney, Agent, or Firm* — Todd A. Lorenz

(57) ABSTRACT

The invention relates to an actuator apparatus (1) for generating the motion of a tool, in particular for the work on biological cell material, which provides at least one electrically controlled actuator element (3), a motion section (3a), at which a tool can be arranged and which is linked to the at least one actuator element, an electrical control device (11) for controlling the at least one actuator element, an electrical measurement device (12), which is configured to perform a measuring method for measuring at least one electrical capacitance quantity of the at least one actuator element, wherein the capacitance quantity is usable to provide information on the status of the actuator apparatus. Further, a corresponding method for obtaining and utilizing said information on the actuator apparatus is provided.

12 Claims, 5 Drawing Sheets

(56) References Cited

U.S. PATENT DOCUMENTS

| | | | |
|---|---|---|---|
| 2003/0094882 A1* | 5/2003 | Mizuuchi | H01L 41/042 310/317 |
| 2006/0010968 A1* | 1/2006 | Munekane | B25J 7/00 73/104 |
| 2006/0192116 A1 | 8/2006 | Baur et al. | |
| 2010/0194408 A1* | 8/2010 | Sturmer | G01N 27/22 324/664 |

FOREIGN PATENT DOCUMENTS

| | | | |
|---|---|---|---|
| JP | 2008284686 A | 6/1988 | |
| JP | S63134836 A | 6/1988 | |
| JP | H01264575 A | 10/1989 | |
| JP | S64064381 A | 10/1989 | |
| JP | H07159698 A | 6/1995 | |
| JP | H09322566 A | 12/1997 | |
| JP | H11305145 A | 11/1999 | |
| JP | 2002134804 A | 5/2002 | |
| JP | 2004120894 A | 4/2004 | |
| JP | 2006000660 A | 1/2006 | |
| WO | WO 2008046051 A2 | 4/2008 | |

OTHER PUBLICATIONS

Xin Ye, Piezoelectric-ceramic-based microgrippers in micromanipulation, Beijing Institute of Technology, 2010, 18 pages.*

Machine translation of DE 19652807, Verfahren und Vorrichtung zum Ansteuern eines kapazitiven Stellgliedes, Jun. 25, 1998, 3 pages.*

* cited by examiner

ACTUATOR APPARATUS WITH CONTROL DEVICE

The present invention relates to an apparatus and a method for generating a tool motion, in particular for the work on soft biological cell material, which provides a control device. Such an actuator apparatus is described by U.S. Provisional Patent Application No. 61/289,669 filed Dec. 23, 2009, naming as inventors A. Graff, J. Lembke and A. Schirr, titled "Apparatus and method for generating a tool motion", which is incorporated herein by reference in its entirety for all purposes.

Such apparatus are known from the use in biomedical applications, for example, in particular for the enucleation and nucleus transfer of cells. In the field of in-vitro-fertilization (IVF) of human or animal cells, a method is known, the so called Intracytoplasmic sperm injection (ICSI), which is an in vitro fertilization procedure in which a single sperm is injected directly into an egg cell (oocyte). The oocytes of mice or rats typically have a diameter of 100 to 120 µm. This relatively large cells allow to mechanically treat the involved biological components. The ICSI method is performed under a microscope using micromanipulation devices, comprising micromanipulators for a precise positioning, micro injectors for applying pressure or feeding small volumes in the order of few micro-liters, for example, and micro capillaries for guiding the flow path of small volumes and for making contact with living cells, in particular. The oocyte is stabilized by a holding capillary with the gentle suction applied by a micro injector. From the opposite side a thin, hollow glass micro capillary, with an opening diameter of typically only few (e.g. 7) µm, is used to collect a single sperm, having immobilized it by cutting its tail with the tip of the micro capillary. The micro capillary is pierced through the oolemma and into the inner part of the oocyte (cytoplasm). The sperm is then released into the oocyte. During the ICSI, the oocyte has to be penetrated by the micro capillary.

Hereby, the outer protection hull of the oocyte, the zona pellucida, turns out to be resistant and requires a special apparatus for the penetration. The same is required for the biomedical method of Assisted Hatching, wherein the zona pellucida is punctually eroded from the outside, to facilitate the hatching of the developing embryo. Other apparatus are used and adapted for the dissection of soft cell material, for example, tissue.

Whenever biological structures like cell membranes or chromosomes are micromechanically treated by an actuator apparatus, e.g. by piercing or cutting motions, a high working precision is desired. However, actuators and electrical connections may show alterations in their properties on a long-term or short-term scale, which reduce the precision of the tool. The loss of precision may lead to failures during certain operations on biological material. Performing ICSI, for example, for injecting a single sperm through the cell membrane of an oocyte to be fertilized requires that the oocyte remains functionally intact. However, the process of piercing the membrane is mechanically sophisticated and can easily lead to an irreversible destruction of the cell membrane, if the ideally one-directional piercing motion is accompanied by interfering lateral motions of the capillary, for example. This way, a single imprecise working step can destroy the biological samples, e.g. costly prepared oocytes or chromosomes, leading to a painful loss of money and time. Further, the loss of precision can result in a slow decrease of effectiveness of the actuator apparatus, which is hardly to recognize by a user, whose productivity may slowly decrease or whose effort has to increase to keep the level of productivity.

Therefore, it is an object of the invention to provide an actuator apparatus and method for working on biological material with the capability to gain information on the status of the actuator apparatus or one of its components.

The present invention achieves said object by providing an actuator apparatus according 30 to claim 1 and a method according to claim 12. Preferred embodiments of the present invention are subject matter of the dependent claims.

The actuator apparatus according to the present invention for generating the motion of a tool, in particular for the work on biological cell material, provides at least one electrically controlled actuator element, a motion section, at which a tool can be arranged and which is linked to the at least one actuator element, an electrical control device for controlling the at least one actuator element, an electrical measurement device, which is configured to perform a measuring method for measuring at least one electrical capacitance quantity of the at least one actuator element, wherein the capacitance quantity is usable to provide information on the status of the actuator apparatus.

The provision of a measurement device for the actuator apparatus allows to obtain and to utilize information on the status of the actuator apparatus, in particular on the status of the at least one actuator element. This way, an improved control of the capability of the actuator apparatus can be achieved, which improves the reliability of the actuator apparatus and the reliability of the applications of the actuator apparatus.

In the present description of the invention, the wording "configuration of a device for a function" or "the device being configured for achieving a function" means that the respective device comprises means, which are adapted for performing the specific functions, e.g., in a way well known for the skilled person, e.g. the electrical engineering technician. The electrical control device or other electrical device providing "means" implies that the device comprises electric circuits, preferably, which provide the specific function. Such means can also comprise a capability for a program- or software control of the respective device, wherein said means can comprise the software or program code, which implements the specific function.

The electrical capacitance quantity can be any physical parameter or value, which can be utilized to measure the electrical capacitance of the at least one actuator element by the measurement method, e.g. time, voltage, charge, current. The electrical capacitance quantity, preferably, is the electrical capacitance of the at least one actuator element. Capacity measurements are particularly sensible to detect errors of the at least one actuator elements or the connectors/cables. This applies, in particular, if the actuator element is a piezoelectric element, which change their extension in dependence on their charge or the applied voltage, and which can be considered to be capacitors.

Preferably, the control device provides means for controlling the actuation of the at least one actuator element according to a motion procedure. No restrictions exist in regard to the means for controlling the actuation. Such means for controlling the actuation can comprise electrical circuits, which adjust the output voltage, which is used to operate the at least one actuator element, i.e. let the at least one actuator element perform an actuation motion. The output voltage can be put out by the control device or by another device, which provides an appropriate supply voltage. Such means for controlling the actuation can in particular comprise switch means, which switch on or switch off the output voltage, in particular, comprise one or more electrical relays or, in particular, comprise an insulated-gate bipolar transistor (IGBT). Further, said means for controlling the actuation can comprise a time measuring device, e.g. based on electrical circuits, which in particular contain an oscillating crystal.

The control device, preferably, provides means for automatically initiating the performance of said measuring method upon initiation of said actuation. This allows several useful configurations of the actuator apparatus. In particular, it allows to further configure the control device such that the result of the measurement, i.e. the value of the electrical capacitance quantity, influences the subsequent control steps for actuating the at least one actuator element. In a preferred embodiment, said influence provides to prevent the control device and/or the at least one actuator element from performing an actuation. For example, the measured electrical capacitance quantity can indicate a failure of one or more actuator elements or a failure of the controlling circuitry. Detecting the failure by means of the measurement allows to prevent the actuation or the output of a possibly high output voltage, respectively, which can save the actuator elements from being further damaged. In particular, measuring the electrical capacitance can detect connection errors between the actuator apparatus and an external control device or can detect cable short-cuts. This avoids situations, where the user of the actuator apparatus applies the apparatus for performing a microdissection or micromanipulation, which uses motion patterns, which are too small to be observed by the eye under the microscope. A system error, which cannot be detected visually, for example, may be detectable by the measurement of the electrical capacitance quantity. This way, the system integrity and safety is enhanced.

Moreover, said step of influencing the subsequent control steps after the measurement in dependence on said capacitance quantity can provide to adjust the output voltage for controlling the actuation of the at least one actuator element to a desired value. For example, the value of the capacitance quantity can indicate the presence of a specific type of actuator element configuration, which is connected to the measurement device or the control device, respectively (referred to as "automatic device detection"). This allows that the output voltage can be adjusted in dependence on the actuator element configuration, for example. For example, the control device could be configured to include a data table, e.g. by using digital electronic means (CPU, digital memory, or microcontroller), which correlates the measured values of the capacitance quantity with a certain type or configuration of the at least one actuator element. The control device can be configured to select a modified control method in dependence on the detected type or configuration of the at least one actuator element, wherein said control method can provide to supply a predetermined type of output voltage for operating the actuator element. Such a feature enhances the system integrity, because it prevents that an actuator element is operated by using inappropriate parameters, e.g., an inappropriate output voltage.

The motion procedure, which controls the actuation of the at least one actuator element, can be initiated after a delay period after having performed, started or finished a measurement of the capacitance quantity, preferably. The control device and/or measurement device provides electrical circuitry for achieving said functionality, preferably. Said delay period is, respectively preferably, shorter than 10 s, 1 s, 100 ms, 10 ms, 1 ms, 100 µs, 50 µs, 10 µs, 1 µs, 100 ns, 10 ns or 1 ns. The provision of the delay period allows that the steps of measuring and actuating be temporally uncoupled, which renders the operation of the actuator apparatus more safe. During the measurement, the at least one actuator element is substantially not charged by a voltage higher than, preferably, 15V, 16V, 20V, 25V or 50V, preferably, which can be achieved by an appropriate configuration of the control device.

The motion procedure is a predetermined motion procedure or a user controlled motion procedure, preferably. A predetermined motion procedure can comprise one or more actuations of the at least one actuator element in a temporal sequence, which lead to a corresponding sequence of tool motions. A user controlled motion can be an actuation or a sequence of actuations, which is initiated and/or stopped by the user via appropriate user interface means, e.g. a pedal or manual switches.

Preferably, the actuator apparatus provides connector means which serve to connect the at least one actuator element to the control device, in particular, for applying a voltage to the at least one actuator element. Such connector means can comprise means for a wired or a wireless connection. The connector means, preferably, are configured for allowing signals to be exchanged between the control device and the at least one actuator element or between the control device and another device, e.g. a power supply or an electrical interface for supply voltage regulation. Moreover, the connector means are configured to provide the supply voltage, preferably, which is used to let the at least one actuator element perform the actuation(s). For example, the connector means can comprise one or more electrical plugs, e.g. a coaxial plug, or one or more electrical cables, e.g. a coaxial cable.

Preferably, the control device provides means for controlling the output voltage, which is put out by said connector means. Such means for controlling the output voltage can comprise electrical circuitry for controlling voltages, e.g. power electronics. Preferably, the control device is configured to apply a first output voltage by default, and to temporarily provide a second output voltage, which is appropriate to let the at least one actuator element perform an actuation, while the first output voltage is not appropriate for achieve the actuation, preferably. The first output voltage can be appropriate to perform the measurement of the capacitance quantity. This offers the advantage that the second output voltage can be applied in dependence on the measured electrical capacitance quantity or in dependence on other signals or events. For example, the first output voltage can be lower, e.g. by a factor of more than 0.5, 0.25, 0.1, 0.05, 0.01, 0.001 or 0.0001, than the second output voltage. In particular, the first output voltage or the second output voltage can be smaller or equal than substantially 50V, 25V, 15V, 12V, 10V, 7.5V, 5.0V, 2.5V, 0.5V or 0.0V, respectively. Such a low output voltage is, in particular, appropriate to prevent that a user, who touches the connector means, e.g. the power supply plugs, of the at least one actuator element, is injured by accident in a case, where the control device is arranged externally from the actuator apparatus. This renders the use of the actuator apparatus more safe. Of course, the output voltage can also be zero. Controlling the output voltages this way enhances the system integrity, because inappropriate output voltages can be avoided.

For example, the measurement device and/or the control device can be configured to detect the connectivity status, in particular the presence or absence, of the at least one actuator element at the control device (or measurement device). In particular, the control device could be configured to conclude from the measured capacitance quantity that no actuator element is connected to the control device, in particular, by measuring substantially a zero increase of the charge upon charging of the at least one actuator element (e.g., a stack of piezoelectric elements), if a test voltage is applied. This case can occur, for example, if the control device is arranged externally from the actuator apparatus and the control device is not connected to the actuator apparatus. The case can also occur, if said connection is broken or short-cut. Thus, detecting the connectivity status enhances the system integrity and safety.

Preferably, a first status and a second status of the actuator apparatus are provided, wherein the control device provides means for changing the actuator apparatus from the first status to the second status in dependence on the result of said measuring. This way, the result of the measurement can be used to influence the actuator apparatus itself, which renders the apparatus more versatile. For example, the second status can be defined such that the actuator apparatus consumes less energy in the second status than in the first status. For example, the power supply could be switched off or be set to a low consumption mode, for letting the apparatus consume a power of less than 25 W, 15 W, 12 W, 5 W or 1 W, respectively. This way, the actuator apparatus can be set to an energy saving mode, which reduces cost and increases life-time of the apparatus.

Further, said second status can be defined such that the actuator apparatus uses a modified control method for controlling the actuation of the at least one actuator element in the second status compared to the first status. This way, the control of the at least one actuator element can be adjusted to correspond to the actual status of the actuator element(s). For example, a modified control method can be used for reducing or eliminating errors or failures of the at least one actuator element. This may be possible assuming that the detected failures are correctable. This way, the constancy of precision in performing the motion of the apparatus can be improved. In particular, the preferred linearity of the tool motion along a linear direction can be maintained or corrected. The control device, in this case, may be configured to calculate control parameters of the modified control method for the required error correction, e.g. calculate the required output voltage, or take the required corrections from a data table.

In a preferred measurement method of the electrical capacitance quantity, the time is measured, or a quantity depending on the time, which is required to charge the at least one actuator element, starting from a starting value, which can be zero, ending at a target value, which can be a reference value, if a constant voltage is applied to the at least one actuator element. Hereby, the charging current can be substantially constant. Preferably, the measurement device comprises means to measure the charge of the at least one actuator element and means to measure the time period, which is needed for the at least one actuator element to charge from a starting value of the charge to a reference value of the charge. Alternatively, the time can be measured which is required for discharging the actuator element(s) from a starting value to a target value.

One or more reference value(s) can be predetermined and can be stored in a memory means of the control device, for example. The reference value can also be detected by performing a reference measurement, using the actuator apparatus or another apparatus. The reference measurement can be performed upon user request or during assembly of the actuator apparatus in the factory.

The measurement device is connected to the control device or at least partially build integrally with the control device, e.g. by sharing components, e.g. the housing or a circuit board. Preferably, the measurement device comprises means to measure the charge of the at least one actuator element and that the measurement device comprises a comparator circuit which compares the charge of the at least one actuator element with a reference value. Further, the control device and/or the measurement device comprises a time measuring device for measuring time periods between electrical signals with a precision of, preferably, at least 1 ns, 10 ns or 100 ns. Moreover, the measurement device can be configured to consider the temperature or temperature changes, which can influence the capacitance of the at least one actuator element. Thus, the measurement device can be configured to compensate deviations caused by temperature drift. Preferably, the actuator apparatus comprises at least one temperature sensor, which is connected to the control device or measurement device.

Other methods for measuring the electrical capacitance quantity are possible and preferred, and can be implemented in the control device or the measurement device, respectively. For example, the actuator element(s) can be charged from a first voltage to a second voltage within a predetermined charging time and the measurement device determines the current charging the actuator element(s), wherein the electrical capacitance quantity is the current or a value, which depends on the current.

The measurement device, preferably, is configured to perform one or more additional procedures, e.g. an initialization procedure, preferably—automatically or user-defined–before starting the measurement of the at least one electrical capacitance quantity, or—automatically or user-defined—after finishing the measurement of said quantity. Said additional measurement is preferably performed while the actuator elements are not connected to the control device. Said additional procedure can be adapted to measure correction parameters or values, which serve to determine more precisely the capacitance quantity by correction. For example, said additional procedure may be adapted to determine offset parameters of the capacitance quantity, which may be caused by drift effects and may be subtracted from the measured capacitance quantity or used for calibration.

Further, said additional procedure may be adapted to measure one or more parasitic capacitance quantities, which have to be regarded for the precise determination of the capacitance quantity to be measured, which also may be subtracted from the measured capacitance quantity or used for calibration. Preferably, the measurement of a parasitic capacitance quantity is measured only once, preferably before delivery of the manufactured actuator apparatus to the customer, or upon user request, using a maintenance program, which can be provided in the control device. The result of the measurement of a parasitic capacitance quantity can be stored in memory means e.g. of the control device, and can be used as calibration parameter for all measurements, which are performed by the measurement device, for regarding parasitic effects of the apparatus, e.g. the parasitic capacitance of a circuit board, one or more IGBT, the diode(s), etc., if applicable.

The invention further relates to a method for obtaining and/or utilizing information on an actuator apparatus, in particular for the work on biological cell material, in particular the actuator apparatus according to the present invention, the method providing the steps:—measuring at least one electrical capacitance quantity of the at least one actuator element of the actuator apparatus; using the measured capacitance quantity to provide information on the status of the actuator apparatus.

Preferred embodiments and further preferred steps of the method according to the invention can be derived from the description of the apparatus according to the invention and its embodiments.

In a preferred embodiment of the actuator apparatus, which is referred to in U.S. Provisional Patent Application No. 61/289,669, mentioned above, the actuator apparatus further comprises an actuated member, which is elastically deformable, the at least one actuator element being linked to the actuated member such that an actuation by the at least one actuator element elastically deforms the actuated member by a distance, which corresponds to a length change of the actuated member, wherein said length change causes said motion of the motion section. Hereby, the motion section is connected to the actuated member, preferably. Many preferred configurations of the actuator apparatus according to the present invention, described in the following, refer to the embodiment of the actuator apparatus comprising an actuated member. However, said configurations can also be applied independent of said preferred embodiment of the actuator apparatus, if applicable.

The apparatus and the method according to the invention are preferably adapted for their use in biological, medical, biomedical or chemical (for example biochemical) applications and the like, preferably for working on soft matter and preferably not adapted for the work on non-soft matter. Soft matter is understood to be matter like biological matter, e.g. tissue, e.g. with a Young's modulus smaller than preferably 10 GPa, 5 GPa, 1 GPa, 0.1 GPa, 0.01 GPa, or 0.001 GPa, respectively. However, the application of the apparatus and the method according to the invention with regard to non-soft matter, in particular for matter with Young's modulus larger than 10 GPa, is also possible. The apparatus and the method according to the invention are preferably used and adapted to be used for IVF, ICSI, Assisted Hatching, Enucleation, Nucleus transfers, Micro chirurgery, Patch Clamp and other biological and medical fields, in particular adapted to be used for working on cells from humans, animals, e.g. mice, rats or bovines, in particular on oocytes, or are adapted to be used for multiple of such applications, respectively. The apparatus is further preferably adapted for performing the Dissection of cell material, e.g. the single cell dissection from paraffin sections, the dissection of areas from histological sections and/or the Separation from stem cell aggregates from 3D-cell cultures. However, the apparatus and/or the method can be used also for other applications, in particular to non-biomedical applications, which in particular require a motion with amplitudes in the nanometer to micrometer range or other ranges and general for those applications, which can benefit from the advantages and features of the apparatus and/or the method according to the present invention.

The motion of the motion section of the apparatus according to the invention can be realized by means of an actuated member, which is actuated by at least one actuator element and which itself actuates the motion section, which is linked to the actuated member. Preferably, one actuation action by the at least one actuator element elastically deforms the actuated member by a distance, which substantially equals to the effected one length change of the actuated member. Preferably, the actuation action of the at least one actuator element leads to a net length change of the actuated member. Preferably, a second length change of the actuated member is caused by substantially the first length change of the at least one actuator element, which performs one actuation action. Said first length change and said second length change preferably take place substantially at the same time. Preferably, there is substantially no phase shift between the motion of the actuated member and the motion of the at least one actuator element. Preferably, the value of the second length change (v_am) and the value of the first length change (v_ae) are the same. This configuration offers the advantage that a preferably direct interaction between the action of an actuator element and the (re-)action of the actuated member is achieved, which allows a more precise control of the motion of the motion section and enables the realization of displacements of the motion section with a controlled number of displacements, e.g. 1, 2, 3, 4, 5, or more definit displacements instead of performing an oscillation motion with an undefined number of oscillations. Preferably, the ratio v_am/v_ae fulfils one of the following conditions, respectively: v_am/v_ae=1; |v_am/v_ae−1|<0.5 or 0.2 or 0.1 or 0.01. Preferably, said net length change has the value v_am.

The apparatus is preferably configured such that a straight line in parallel to the direction of an at least partially linear motion of the motion section (actuated by the actuated member), which runs through the motion section or through the length of an elongated tool, which is mounted at the motion section, does not run through the actuator element or through a part of the actuator element. With such a configuration, the impacts acting from outside on the motion section or on the tool mounted to the motion section do not directly act along a straight force-transferring line on the actuator element. Rather, said impacts and other mechanical loads are at least partially or (almost) completely absorbed by the actuated member.

Most preferred, the apparatus is configured such that a force, which is exerted on the motion section or on a tool, which is mounted at the motion section, in particular, from outside the apparatus, is transferred to the actuated member, substantially, and is further transferred from the actuated member towards a connecting section, substantially, which is preferably provided at the actuated member, and is preferably further transferable via said connecting section to a holder device, which preferably is adapted to hold the apparatus and which is absorbing the force, which was exerted from outside, (almost) completely or at least partially. Therefore, the motion section, the actuated member and the connecting section, and preferably also a potential holder device, are preferably connected in series, forming a direct force transferring chain.

Moreover, the at least one actuator element is preferably mounted at the actuated member such that a force, which is exerted on the motion section or on a tool, which is mounted at the motion section, in particular, from outside the apparatus, is acting on the actuator element by a minimal fraction, only, e.g. a fraction of smaller than preferably 0.001, 0.01, 0.1 or 0.5. Rather, said force is mainly transferred and further distributed by the actuated member, preferably towards a connecting section at the actuated member, and is preferably further distributable to a holder device, which can be provided to hold the apparatus at said connecting section.

Preferably, a force acting on the motion section is distributed between the actuator element (ae) and the actuated member (am) in a ratio force_on_ae/force_on_am, said ratio being preferably smaller than 0.5; 0.25; 0.2; 0.1; 0.5; 0.01; 0.005; 0.001; respectively. This can be achieved, in particular, if the resistance, which counteracts an impact force, which acts on the motion section, is mainly based on the resistance of the actuated member and is less based on the resistance of the actuator element. For implementing this, an arrangement of the actuated member and the at least on actuator element is preferred, which promotes the distribution of said force in a larger fraction on the actuated member and in a lower fraction on the actuator element(s), which is realized by several embodiments of the apparatus according to the present invention, in particular.

Further, the actuated member will provide a larger amount of resistance, if the capability of the same to deform under the application of a deformation energy (e.g., upon an impact force) is relatively low, e.g. compared to the corresponding capability of the actuator element, and is relatively high for the actuator element. Thus, the Young's modulus of the material of the actuated member (Y_am) is preferably relatively high and the Young's modulus of the material of the actuator element(s) (Y_ae) is preferably relatively low. Preferably, Y_ae is lower than the Y_am by a factor of at least 0.9, 0.85, 0.75, 0.5, 0.25, 0.1 or 0.05. For example, it is preferred that 0.85<Y_ae/Y_am<0.90, 0.5<Y_ae/Y_am<0.80 or 0.1<Y_ae/Y_am<0.5.

These configurations offer the advantage that the apparatus is more robust than other apparatus, where the motion section is connected in a straight force-transferring chain directly to the actuator, e.g. a piezoelectric element, which may be damaged upon an unintended impact of the tool to a glass substrate, long-term stress or other mechanical stress, which acts undamped via said line of components on the actuator. The preferred embodiment of the present invention utilizes the actuated element, which buffer impacts, offers a higher structural stability and robustness and makes the method according to the invention more reliable. In such a configuration, the actuated member can be seen to be the "backbone" of the apparatus, which is moved by the actuator element(s), which are preferably mounted in parallel to the actuated member ("backbone"), thus forming the "muscle".

Further, the linkage of the actuator element(s) relative to the actuated member according to the embodiment of the invention allows to use lighter and smaller components, providing a lower total mass of the system, which allows faster actuation changes, and higher oscillation frequencies for the case of an oscillating motion. Moreover, the actuator element(s) can be arranged closer to the motion section, to make the force transfer to a possible tool (capillary etc.) more effective.

Linkage of a first element to a second element in the context of the invention preferably means a kinematical coupling of both parts, preferably where the motion of the first element results in a motion of the second element. Linkage and "to be linked" can mean that both parts are permanently or non-permanently fixed to each other in all dimensions or at least one or two dimensions, e.g. by integrally forming both parts or by a connection from at least one of the types force-closure, form-closure or adhesive bond. Linkage of a first part and a second part further includes the case that the first part is linked to the second part via a third part or further parts, wherein for example the first part is linked to the third part and the third part is linked to the second part. Here, for example the first part can be the actuator element, the second part can be the actuated element and the third part can be one or more connecting means. For the apparatus and the method according to the invention, it is preferred that linkage of the components is such that a play between the components is avoided. In particular, no floating bearing has mandatory to be utilized for the apparatus. This makes the design of the apparatus less costly and improves the accuracy of the generated motion and the capability of the apparatus.

The motion section is preferably integrally built with another part of the apparatus, e.g. integrally built with the at least one actuator element or the actuated member. The at least one actuator element or the actuated member preferably extends along a central axis, and the motion section preferably is arranged at the actuated member such that said axis extends through said motion section. In particular, the motion section is the section of the apparatus, which is adapted for mounting a tool, preferably.

The motion section is preferably adapted to permanently or removably carry or connect or hold a further element, in particular a tool, e.g. a microdissector needle or a capillary, said tool preferably made from metal, glass or plastic.

Preferably, a mounting head for removably mounting a tool is firmly connected or connectable to the motion section, such that the motion, which is supplied by the apparatus, in particular by the actuated member, is preferably completely, but preferably at least partially, transferred to the tool in order to move the tool. The mounting head may comprise connecting means for connecting an element, e.g. the tool, to the mounting head. The connecting means may comprise a thread, a means for latching, a magnet and/or the like. The mounting head can be formed integrally with another part of the apparatus, e.g. the actuated member or a carrier. A second mounting head is preferably provided to be removably connected by second connecting means with the first mounting head to allow using different second mounting heads, which are respectively adapted to hold a specific type of element, e.g. tool, for example the type depending on the outer diameter of a capillary or needle.

The mounting head can be adapted to form at least one channel, such that a fluid may flow through the mounting head. This can be useful to apply pressure or low-pressure, if for example a capillary is used as a tool, to use said pressure changes and a controlled pressure to work on the target material, e.g. the cell. The use of channels is preferred for the use of the apparatus in combination with a microinjector or for patch clamp applications, where an electric contact is made via the conductive electrolyte in the channel, or for other applications, where channels are useful. Further, the optional second mounting head can be adapted to form a channel, such that a fluid may flow through the mounting head. If required, sealing means, e.g. O-rings from plastic, are provided to seal the interior of said channel relative to the exterior, in particular to seal the channel at the junction sites, where two channel parts are connected.

The actuated member preferably is the part of the apparatus which can be actuated by the actuator element and is the part of the apparatus, which serves as the actuator which moves the motion section.

The actuated member preferably is a base part or part of a base part, which preferably carries other components of the apparatus. For example, the base part can be the carrier of the at least one actuator element and/or of any linking means, which link the actuator element(s) to the actuated member at its first and second position. Preferably, the actuated member is an integrally formed part. However, it is also possible and preferred that the actuated member comprises at least two parts or more, which are linked to each other, preferably fixed to each other in all three dimensions.

The actuated member preferably provides at least one channel, such that a fluid may flow through the actuated member. Also here, this can be useful to apply pressure or low-pressure, if for example a capillary is used as a tool, to use said pressure changes and/or a controlled pressure to work on the target material, e.g. the cell. If required, sealing means, e.g. O-rings from plastic, are provided to seal the interior of said channel relative to the exterior, in particular to seal the channel at the junction site. The channel can be adapted to be filled with gas, liquids, in particular to be filled with cell plasma, culture medium, water, solution, or with mercury, Fluorinert™ or silicon oil. However, providing a channel or a filled channel is not mandatory but optional for the apparatus and the method according to the invention.

The actuated member may be a bar part or a tubular part, which preferably extends along a (virtual) axis and which preferably is at least in part built symmetrically in relation to said axis. Preferably, the actuated element is an elongated device, where the length is larger than the height or the depth, respectively, and a virtual axis runs through the actuated member, in parallel to its length; further the actuator elements are arranged to act along a second virtual axis, substantially, to mainly generate a linear motion of the actuator element(s) in parallel to said second axis; the actuated member and the at least one actuator element are preferably arranged such that the first axis and the second axis are parallel or coaxial. Further preferred, the net force vector, which results from the motion of said actuator element(s) in parallel to said second axis, matches with the center of area or centroid of a cross section of the actuated member, said cross section taken preferably perpendicular to said first axis, which preferably applies for all possible cross sections or at least the majority of cross sections of the actuated member. This offers the advantage, that the actuated member will just be elongated but substantially not bended, which results in small cutting or drilling width of the tool. Preferably, the actuated member is, or comprises, a hollow-cylinder shaped part or a tube, forming a channel. A tube or a channel offers the advantage that pressure or under-pressure can be applied to an appropriate tool, e.g. a capillary, to mechanically treat the target soft material of the sample, e.g. the cell, by pressure or by injecting volumes of injection material, e.g. a sperm, to the target material (e.g. a cell), or to remove volumes of the target soft material from the sample. It is preferred that said tube or channel is filled with a fluid, which preferably is a gas, e.g. air, a liquid, e.g. Fluorinert®, or mercury.

The actuated member preferably comprises third connecting means, which are preferably built integrally with the actuated member, for connecting or linking other parts, e.g. the at least one actuator element, to the actuated member. A position, at which such a third connecting means is preferably linked to the actuated member, is said first and/or second position, at which the at least one actuator member is preferably linked to the actuated member.

Said third connecting means may comprise at least one projection or at least one recess, which preferably is arranged circumferentially at the actuated member around the axis, along which the actuated member extends. Preferably, the third connecting means comprises a projection, a recess or a step in the outer surface of the actuated member, which preferably respectively provides an engagement site for the engagement of complementary formed connecting means.

The actuated member preferably provides a first position and a second position, wherein the actuated member preferably extends along, preferably extends in parallel to a distance between said first position and said second position and preferably extends in parallel to a straight distance, defining an axis, between said first position and said second position. Between said first and said second position, the actuated member is preferably formed such that an increase or decrease of said distance preferably expands or compresses the material of the actuated member along said distance, preferably without bending it or preferably by additionally bending it. The straight distance between said first and said second position is preferably between 5 and 100 mm, preferably between 5 and 50 mm, preferably between 10 and 50 mm, preferably between 10 and 30 mm, preferably as well in a first status, where the actuated member is not elastically deformed as well as in a second status, where the actuated member is elastically deformed. Preferably, said distance is used only for expansion of the actuated member to expand the actuated member along the length of said distance. Having said elastical deformation applied directly to the actuated member, which preferably forms the backbone of the apparatus, offers the advantage that the dimensioning of the apparatus can be kept smaller if compared for example with the known apparatus with U-shaped base. Further, the provision of an internal expansion distance in the apparatus offers the advantage that the operation is more independent from the suspension of the apparatus, which may be connected to other micromanipulators with linear motors etc., thus allowing more flexibility for the application of the apparatus.

The actuated member preferably is non-deformed in its first status, deformed in its second status and less deformed in a third status. In the third status, the actuated member preferably is less deformed than in the second status by a factor of at least $10^2$, $10^3$ or $10^4$ or different. In the third status, the at least one actuator element preferably is hold under elastic mechanical stress, preferably under compression, by means of the actuated member. The compression, preferably a bias compression, is preferably chosen such that at no time of the operation of the apparatus the actuator element gets under tensile stress. Said compression, for example, can result in a bias force of 1025 N, if the fastening torque of the counter support, which compresses the actuator element, is 500 Nmm, in an idle state of the actuator element. This can be achieved by the connecting means, e.g. comprising a thread, which preferably fix the actuator element to the actuated member, which preferably carries said components. The benefit of such a bias stress is that a play between the actuator element and the actuated member can be avoided in all of its status. Therefore, the force of the actuator element can immediately and directly be transferred to the actuated member. If the actuator element comprises a piezoelectric element, the bias compression in particular leads to an increased load capability of the piezo element. The ability to work under pressure for piezo elements is much higher than to work under tension, sometimes 10 to 20 times higher. Besides the risk of a brittle failure, there is a risk of depolarising the piezo elements, when it is under tensile stress with the wrong voltage. When driving piezo elements under a permanent (bias) compression, the mechanical load capability can be increased compared to a system with mixed tensile/compressive status and higher frequencies of alternate supply power can be applied. A main advantage of providing a bias force is that a faster forward and backward motion of the motion section can be achieved. The motion section can be returned by a fast voltage shift without having the risk of a depolarisation of the actuator element (e.g. Piezo element), which can arise in the case of a tensional load.

The actuated member is preferably made from an elastic material or at least partly made from an elastic material or comprises sections made from an elastic material. Further, the actuated member preferably comprises sections of different elasticity. Said elastic material has a Young's Modulus of preferably larger than 0.2 kN/mm$^2$, preferably larger than 100 kN/mm$^2$, preferably larger than 200 kN/mm$^2$ and preferably between 180 to 240 kN/mm$^2$. Preferably, said elastic material is or comprises steel, ceramics or glass. Steel or other material with Young's Modulus of preferably larger than 180 kN/mm$^2$ offer the advantage that stable structures, in particular stable actuated sections can be designed. This allows in particular to construct more robust and durable apparatus and to provide more reliable methods for generating a motion. On the other hand, such materials are appropriate to be compressed or expanded due to their elasticity, preferably be means of an actuator element, which comprises conventional piezoelectric elements as actuator members or other piezoelectric elements. Preferably, the actuated member is used as electrical conductor and preferably is used as electric circuit component of the apparatus.

The length change of the actuated member in relation to any direction, which is induced by the actuation of the at least one actuator element, preferably corresponds to the difference of straight distances between said first position and said second position, when they are respectively measured in the deformed second status and the non-deformed first status of the actuated member. By definition, for an expanded actuated member, the length change has a positive sign and for a compressed actuated member, the length change has a negative sign in relation to said direction. The length change of the actuated member preferably is taken of the group of ranges of length changes, comprising 0.5 to 2.0 µm, 0.5 to 1.0 µm, 0.1 to 0.5 µm, 0.05 to 0.5 µm, 0.01 to 0.5 µm, 0.01 to 1.8 µm or different.

In all embodiments of the actuator apparatus, namely embodiments with or without an actuated member, said amplitudes are preferably realized by providing at least one appropriate actuator element. An actuator element preferably provides at least one piezo element, and it is preferred to drive said actuator element in a voltage regime of preferably 200V to 425V, 200V to 600V, or 100V to 300V, respectively. Applying to said actuator element a respective voltage, an amplitude can be realized, wherein no bias compression is applied in this case, as described exemplarily by the following example reference list (voltage [V]; amplitude [µm]): (700; 1.1032), (600; 0.9456); (425; 0.6698), (200; 0.3152), (300; 0.4728), (100; 0.1576). Under a bias compression, the amplitudes can be expected to be slightly smaller, e.g. smaller by less than 5.0, 1.0 or 0.01%.

The maximum length change may depend on the length of the actuated section or in particular on said straight distance, and on the strength of the at least one actuator elements which are employed. For a given force, elastic material with higher Young's Modulus will provide a lower length change.

The motion section is preferably linked to the actuated section such that the length change of the actuated element in a defined direction results in the motion of the motion section by an amplitude, which corresponds (preferably equals) to said length change. An amplitude of for example 50 to 250 nm can be used for ICSI, which is e.g. performed on bovine oocytes, in particular for penetrating the zona pellucida with a glass capillary having a few µm (e.g. 5-8) diameter opening. Steel or other material with Young's Modulus of preferably larger than 180 kN/mm$^2$ can provide such appropriate amplitudes, which allow to precisely work on biological cell material or on other structures.

Said elastic material preferably is homogeneous, preferably seen on a macroscopic scale in the order of 1 or 10 µm, or has at least homogeneous sections. Further it is preferred that said elastic material is not homogenous or comprises at least inhomogeneous sections. For example the material can have a structure, e.g. a grain size in the micrometer regime as the typical structure variable or a structure with structure values larger than a micrometer or millimeter. The elastic material can be made from a solid material, which can have hollow sections filled with gas of any pressure, said hollow sections preferably being pores or openings or the like.

The optional bending of the actuated member, which extends e.g. along the x-direction, by a force acting in x-direction can cause a change of the position of the motion section in x-direction. However, for the present invention it is preferred that the length change of the actuated member due to its elastic deformation upon actuation by the actuator member in x-direction is preferably the dominant effect, which shifts the motion section in x-direction, wherein the bending is preferably negligible. This is preferred in particular for the preferred case of a desired linear motion of the motion section. However, bending of the actuated member may also be intended to a certain amount, in particular to generate a motion in more than one direction, for example, at least partially also in x-, y- and/or z-direction. If a linear motion of the motion section is desired, it is preferred that the at least one actuator element is linked to the actuated member such that (substantially) no bending of the actuated member upon actuation by the actuator member occurs in said direction. If a linear motion of the motion section is intended, it is preferred that said bending is preferably negligible. Negligible means tolerable for achieving the desired technical aims of the application of the apparatus, e.g. for performing ICSI. Preferably, a linear motion provides a ratio R of the maximal amplitude $A\_y$ ($A\_z$) of the motion section or the distal tip of a tool, elongated with its proximal end to the motion section, in y-direction (and/or z-direction, respectively) in comparison with the maximal amplitude $A\_x$ in the preferred x-direction, with $R=A\_y/A\_x$ and/or $R=A\_z/A\_x$ being respectively preferably smaller than 0.5, 0.2, 0.1, 0.05, 0.01, 0.005, 0.001, 0.0005, 0.0001, more preferably 0.00005, 0.00001, 0.000005, 0.000001, 0.0000005, 0.0000001.

Further it is preferred that at least one actuator element is linked to the actuated member such that the bending of the actuated member upon actuation by the actuator element occurs with a limited amount in the direction of the motion, said direction being preferably the direction of the length change of the actuated member due to its elastic deformation upon actuation by the actuator member. A limited amount means that the first fraction, by which said bending of the actuated member shifts the motion section in the desired linear direction is small to the second fraction, which is due to the length change of the elastic deformed actuated member in said direction. Preferably, the quotient of the first fraction divided by the second fraction is smaller than 2 or smaller than 1, and respectively preferably smaller than any of the values 0.5, 0.1, 0.01 or 0.001.

At said first or second position, the at least one actuator element is preferably linked to the actuated member such that the actuated member undergoes said length change upon actuation by the actuator element. The first position can comprise or can be a point or a contact area or several points or contact areas, where an element, which transfers the force generated by the actuator element, e.g. the actuator element itself, contacts the actuated member or is linked to the actuated member, in particular to transfer a force generated by the actuator element to the actuated member. Preferably at least a third position is provided on the actuated member, at which an actuator element is linked to the actuated member.

Preferably, the actuation of an actuator element, which is linked to the actuated member, causes a length change of the actuated member along a linear distance between said first position and said second position. Preferably, the actuated member is adapted to be expanded between said first position and said second position by the length of a first length change. Further preferred, the actuated member is adapted to be compressed between said first position and said second position by the length of a second length change. Further preferred, the actuated member is adapted to be expanded between said first position and said second position by the length of a first length change and at the same time is adapted to be compressed between a third position and fourth position by the length of a second length change. Such an adaptation can be realized by configuring the actuated member at said positions to provide counter supports (e.g. projections, recesses, openings, steps) for the linkage of the at least one actuator element to said positions.

At least one actuator element is provided. Preferably multiple, e.g. two, three, four, five six or more actuator elements are provided. Each actuator element preferably comprises at least one, preferably multiple, e.g. two, three, four, five, six or even much more, like several tens or hundreds of actuator members. Preferably at least two or three actuator elements are provided to allow the actuation in x-, y- and z-direction of a coordinate system and which can be, in particular, arranged around the actuated member to allow the actuation of the actuated member in x-, y- and z-direction of a coordinate system.

An actuator element or actuator member can be a piezoelectric element, e.g. a piezoelectric ceramics, e.g. soft- or hard-ceramics, e.g. BaTiO3, PbTiO3, Pb[ZrxTi1−x]O3 (0<x<1; PZT), KNbO3, LiNbO3, LiTaO3, Na2WO3, Ba2NaNb5O5, Pb2KNb5O15, PMN or the like.

Preferably, an actuator element or an actuator member has a ring-shaped structure, preferably a symmetrical circular-ring structure, such that it is arrangable around the body of a cylindrically shaped actuated member. Preferably, at least one actuator element and/or at least one actuator member (e.g. a piezoelectric foil) are stacked together to form one actuating device. The actuator elements and/or the actuator members are preferably arranged in a sequence with respect to at least one direction, e.g. the x-direction. Strong piezoelectric elements are preferred, which e.g., based on PbTiO3, Pb[ZrxTi1−x]O3 (0<x<1; PZT). Stacked Piezoelectric elements are preferred, comprising a stack of some tens to hundreds of individually connected piezo elements, e.g. piezo foils. Preferably, the actuator elements and/or the actuator elements are connected in parallel. This allows to keep the supply voltage relatively low, preferably under 600 V and more preferably under 500 V. Further, the achieved amplitudes of motion are as high as e.g. 0.5 to 1.8 μm and the control electronics are easier and cheaper to realize.

Preferably, the at least one actuator elements is/are arranged such around an axis through the actuated member, that the force vector resulting from the equal actuation of all actuator elements points in the direction of said axis. This is e.g. the case for circular shaped ring-piezo elements, which are arranged around a cylindrical shaped actuated member. This offers the advantage of a linear actuation of the actuated member and motion of the linked motion section in one well defined direction, e.g. the x-direction, which is desired for many applications, e.g. ICSI. Preferably, the at least one actuator element and connecting means, which link the actuator element to the actuated member, are arranged such that the force of the actuator element is transferred axial to the actuated member. This means that under equal control of all actuator element, their net force is acting on the center of the cross section of the actuated member. This offers the optional advantage that a bending of the actuated member is avoided. Thereby, the deflection of an optionally connected tool is reduced such that the section width or the bore diameter is reduced, because preferably only a linear motion is reached. However, it is possible and preferred that for certain applications a bending of the actuated member is allowed by differently controlling the at least one (e.g. two or three) actuator element, to achieve a more dimensional motion.

Preferably, the apparatus comprises connecting means for connecting the apparatus to a second apparatus, which can be a micromanipulator or a suspension device. Preferably, the actuated member is provided with a connecting section, which can be the part of the actuated member which is arranged opposite to the motion section, such that the actuator elements is/are arranged between the motion section and the connecting section, but however, preferably in parallel to the actuated member. Further, it is also possible and preferred to provide a housing for the at least one actuator element, wherein then said connecting means can be arranged to the housing. Preferably, an inert mass element is provided on the apparatus, which is preferably arranged in a force transfer chain between the at least one actuator element and said connecting means, which connect the apparatus to other apparatus. Said inert mass element preferably is made from steel or other material. The function of the inert mass element in this case is to distribute the forces resulting from the actuator element in favour of the propulsion of the motion section, which preferably is the front part of the apparatus and to reduce the propulsion of the connecting means (or the optionally connected other apparatus, e.g. suspension device), which are preferably forming the back part of the apparatus. This follows the concept of Newton's third law "actio=reactio", which means that higher masses are accelerated less than the connected lower masses, resulting in a larger displacement of the lighter mass (the motion section) compared to the displacement of the larger mass (the inert mass element and the optional connected further apparatus). Thus, the generation of the motion is more efficient and the junction of the apparatus to preferably connected further apparatus as well as the further apparatus is less stressed.

Preferably, a control device is provided for the apparatus, which controls the actuation by the at least one actuator element. The control device preferably comprises electric circuitry, in particular power circuitry for controlling the supply power of the actuator element. Such circuitry preferably comprises an insulated-gate bipolar transistor (IGBT). The high voltage, which is supplied by a supply voltage generating means, preferably is distributed to the piezoelectric elements with the desired amplitude and frequency by means of an IGBT. The control device preferably comprises a microcontroller, preferably a microprocessor and preferably data storage devices, e.g. RAM, ROM or EEPROM or the like. The control device preferably is adapted to be programmable by the user of the apparatus to preferably implement predetermined motion programs, according to which a motion is generated in a desired sequence, frequency, pulse number, amplitude and the like, to improve the reproducibility of the work with the apparatus. The control device preferably is externally arranged, in particular mounted externally, from the apparatus according to the present invention and preferably connected to the apparatus via cable. However, it is also possible and preferred that the control device is linked or mounted to the apparatus.

The control device, preferably, includes the measurement device. This can be realized by providing one housing for the control device and the measurement device. Moreover, it is possible that the control device and the measurement device share components, e.g. a CPU, memory means or one or more circuit boards.

Preferably, the apparatus comprises input means to receive signals and/or output means to send signals. The input means can comprise buttons or a control panel or the like for the user control of the apparatus. The input means can also comprise a data interface to remote control the control device by another device, e.g. a workstation or PC, for automization of the work with the apparatus. In particular, a foot switch may be provided, preferably as one of said input devices, to allow the user to take control by his feet. The foot switch may be connected to the apparatus or to an external control device. The output means may comprise visual and/or acoustical means, e.g. loudspeaker or displays or LEDs, wherein the control device is adapted to signal information on the status of the control device or the apparatus to the user. The output means can further comprise a data interface to send information to another data processing device, e.g. to a workstation or PC. Also the apparatus can comprise a control device and/or input means and/or output means, in particular a data interface, to provide information on its status and the status of the actuator elements, e.g. the piezoelectric elements. This allows to monitor the operation and the capability of the apparatus.

The control device is preferably configured to control the actuation of the at least one actuator element. Preferably, the control device is adapted to let the at least one actuator element perform a number of actuation actions during a motion procedure, which can be chosen by a user or can be chosen automatically, said number being preferably 1, 2, 3, 4, 5, or larger. Preferably, the control device is adapted to supply all actuator elements with the same power. However, it is also preferred that the control device is adapted to supply different actuator elements or actuator members with different power, preferably according to a predetermined program, which preferably is stored in a data storage of the control device. Preferably, the control device is adapted to control the motion of the motion section. Preferably, the control device is adapted to generate single pulses or single impacts or a sequence of propulsions of the motion section with a predetermined or user definable number of pulses, oscillatory motions or motion patterns with different motion amplitudes, frequencies, delay times etc.

Moreover, further advantages, features and applications of the present invention can be derived from the following embodiments of the apparatus and the method according to the present invention with reference to the drawings. In the following, equal reference signs substantially describe equal devices.

Figure 3:
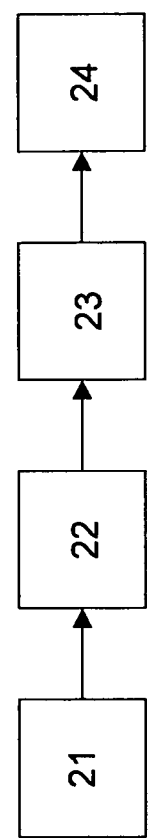

FIG. 3 schematically shows an embodiment of the method according to the invention.

Figure 4:
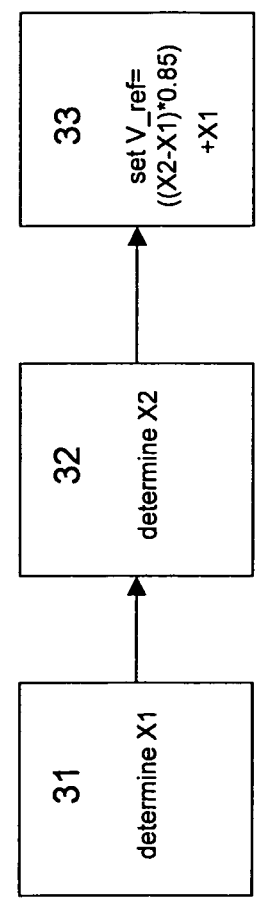

FIG. 4 shows a method step of obtaining a reference value for the method shown in FIG. 3.

Figure 5:
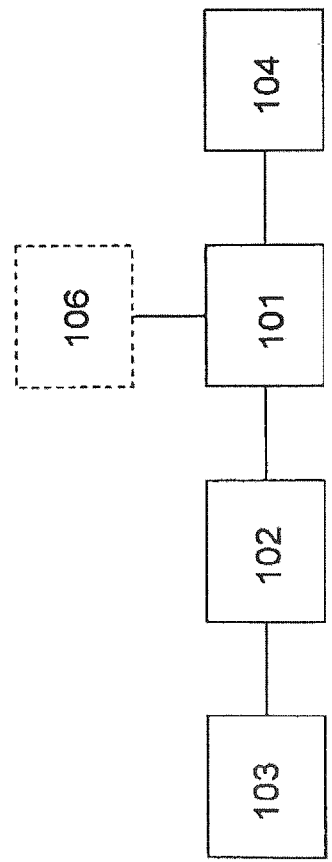

FIG. 5 shows a block diagram of a system with some functional components comprising any embodiment of the actuator apparatus according to the present invention.

The following embodiments of the actuator apparatus according to the present invention relate to a "cell driller", which is the apparatus adapted to drill holes into the membranes or hulls of biological cells, as required for example for performing ICSI. The term "driller" does not mandatory imply a rotational motion of a tool, which can be connected to the driller, but may imply rotational motion.

Figure 1:
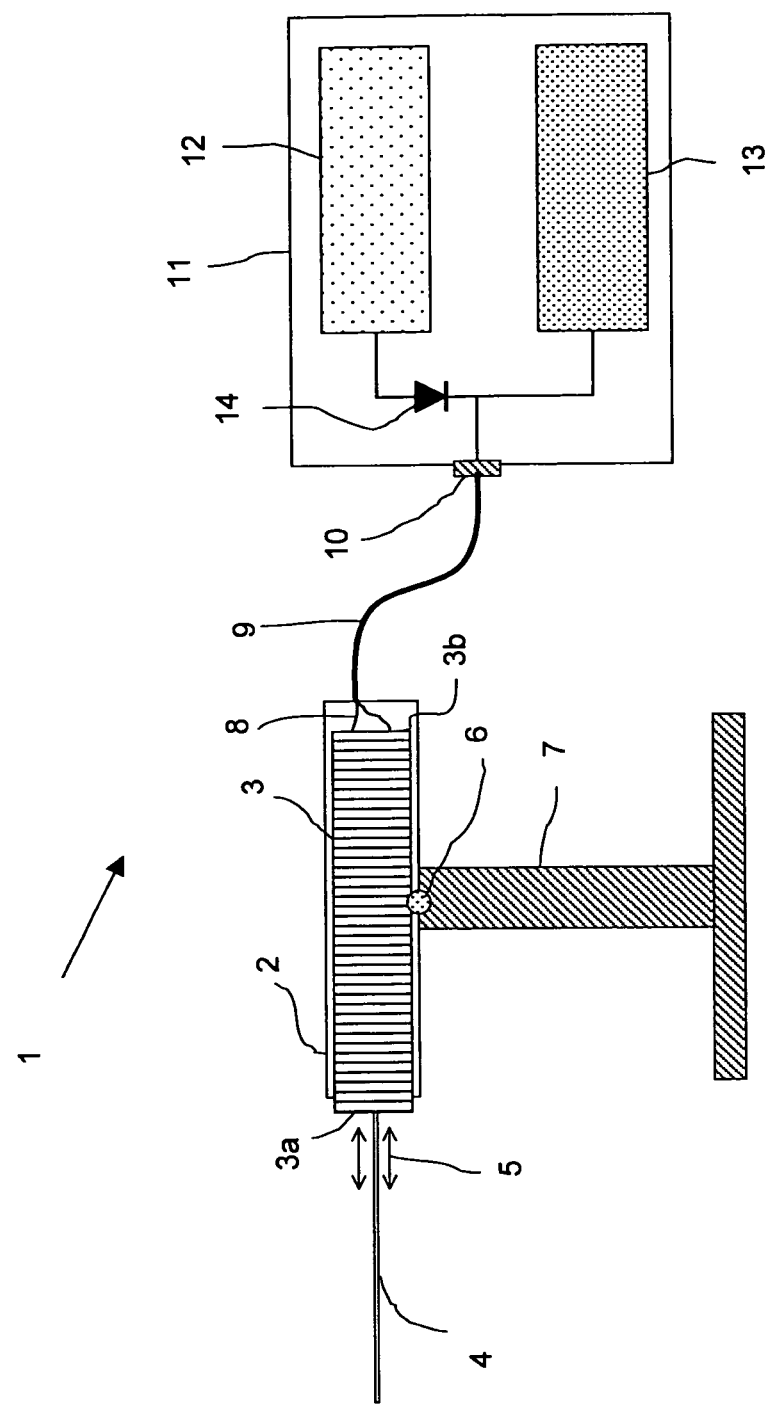
FIG. 1 is a schematic drawing, which shows a preferred embodiment of the actuator apparatus according to the invention.

FIG. 5 shows a block diagram of a system with some functional components comprising any embodiment of the apparatus according to the present invention, which is operated according to any preferred configuration of the method according to the invention. The cell driller 101, which can be the actuator apparatus shown in FIG. 1, is preferably used for the overall system (101; 102; 103; 104; 105; 106). The cell driller is suspended and hold by a micromanipulator 102, e.g. the Eppendorf TransferMan NK 2™. The micromanipulator 102 is mounted to an inverted microscope 103, e.g. the Nikon Eclipse Ti™.

The cell driller 21 is controlled via the external control device 104. The latter comprises a control panel and two foot switches connected to it. Alternatively, a hand switch may be used with at least two switches. The operation of the first foot switch (channel 1) triggers the start of a pulse sequence, where the tool of the cell driller 101 is linear moved forth and back according to parameters which are appropriate to penetrate the zona pellucida (zona) of an oocyte. The second foot switch (channel 2) triggers a pulse sequence appropriate to penetrate the oolemma of an oocyte. The set of parameters for both channels is determined according to respectively three single parameters: the amplitude (a) of the impulse of the tool, the number (n) of impulses in one sequence and the frequency (f) or delay time which define the temporal sequence of the impulses.

For penetrating the zona or the oolemma, the following sets of parameters are useful:

Zona:
a=preferably 0.20 to 0.95 μm, preferably 0.20 to 0.67 μm;
n=preferably 1 to 70, preferably 1 to 10;
f=preferably 1 to 40 Hz, preferably 1 to 10 Hz.

Oolemma:
a=preferably 0.12 to 0.5 μm;
n=preferably 1 to 20, preferably 1 to 5;
f=preferably 1 to 40 Hz, preferably 1 to 10 Hz.

The optimal choice of parameters depends on the type of cell, which has to be penetrated. It further depends on the capillary, which is used as a tool, and its potential filling material, which can be Fluorinert™ FC-77 or mercury. Therefore, the optimal parameters can be different from the ranges of the parameters described here. Preferably, the apparatus, i.e. the cell driller 101, is adapted to tolerate other parameters. For example, it can be possible to several times start a sequence of impulses to succeed in penetrating a specific membrane.

In addition to the cell driller function, the embodiment of the cell driller 6 described here also offers a second function and can be used as microdissector to dissect cell membranes or tissue. If the dissection mode is started via the control panel, the parameter n is preferably not selectable. Instead, the dissection tool is preferably controlled by operating the foot switch until the switch is released. It is possible to perform a norm frequency dissection with f=0 to 1000 Hz or a high frequency dissection with f=20 to 40 kHz.

Moreover, the apparatus according to the invention, in particular the cell driller 101, and/or the control device, in particular the control device 104, is/are adapted to provide a clean function, which aims to clean the tool from adhering material, e.g. cell material. The clean function can preferably be started by the control panel or by "double clicking" a foot pedal. The cleaning method provides a sequence of impulses, which is appropriate to shake off cell material at clean-frequencies, preferably between 2 to 10000 Hz, 10 to 2000 Hz, 100 to 2000 Hz, 800 to 1200 Hz, 950 to 1050 Hz or different frequencies.

If the cell driller 101 is used for the injection of material into a cell (e.g. ICSI), the apparatus requires besides the interfaces to the control device 104 and to the micromanipulator 102 also a third interface to the microinjector 106, e.g. the Eppendorf CellTram Oil™. The microinjector 106 doses smallest volumes of liquid, e.g. 100 to 1000 $\mu m^3$ or different, to the capillary, in particular the volume occupied by a single human sperm of about 380 $\mu m^3$ which is moved by the cell driller 101. If instead of a capillary a microelectrode is used as a tool, then the microelectrode has to be provided by an appropriate control device. If the cell driller 101 is used for the micro dissection of a tissue sample, then the microinjector 106 or a controller for a microelectrode can be omitted or disconnected.

FIG. 1 shows an embodiment of the actuator apparatus 1 according to the present invention. The actuator apparatus is a cell driller, as described above with reference to FIG. 5. The actuator apparatus generally provides the actuating device (2, 3, 4), which is fixated by a stand 7 and adjustable link means 6 for changing the position of the device (2, 3, 4), and the control device 11. The actuating device comprises a stage or housing 2, which holds the actuator elements 3. The actuator elements 3 comprise a stack of piezoelectric elements, which are connected in series to act as a single actuator element, which moves the actuated section 3a (the motion section) of the actuator element 3 in a linear forth- and back motion along the direction, which is symbolized by the double arrows 5. The mounting section 3b of the actuator element is fixated to the housing 3. The tool 4, e.g. a glass capillary, is mounted to the motion section 3a and moves with the motion section.

It is preferred that the actuating device comprises an elastic actuated member (not shown), e.g. a steel tube, which is deformed by the actuator element 3, the actuated member carrying the motion section at a front face, which is thus indirectly actuated by the actuator element via the elastic deformation of the actuated member.

The actuator element 3 is controlled by two connections 8, which can apply voltage to the piezoelectric elements 3 for actuating the same or which can apply a test voltage for performing a measurement of the electrical capacitance quantity of the piezoelectric elements 3. The two connections 8 are connected to the coaxial cable 9, which is connected to the coaxial plug 10 to the control device 11.

The control device 11 is an external control device, being mounted externally from the actuating device, in particular externally from the housing 2 of the actuator elements 3. The control device 11 contains the measurement device 12 and the actuation control device 13, which are described with reference to FIG. 2. The diode 14 protects the measurement device 12 during the actuation against the high supply voltage of the piezoelectric elements.

The control device 11 can comprise other components, not shown. For example: a microcontroller, a CPU, data memory means for storing operational data, e.g. reference values for the capacitance quantity or program data for automatically performing a user requested motion procedure, data connections, power electronics, user interfaces, e.g. input/output devices, data interfaces for connection with an external PC, e.g. used for the exchange of operational data or of a data log file, which was saved by the actuator apparatus automatically during previous measurements of the capacitance quantity, for example, and which can be used for further diagnose purposes.

Figure 2:
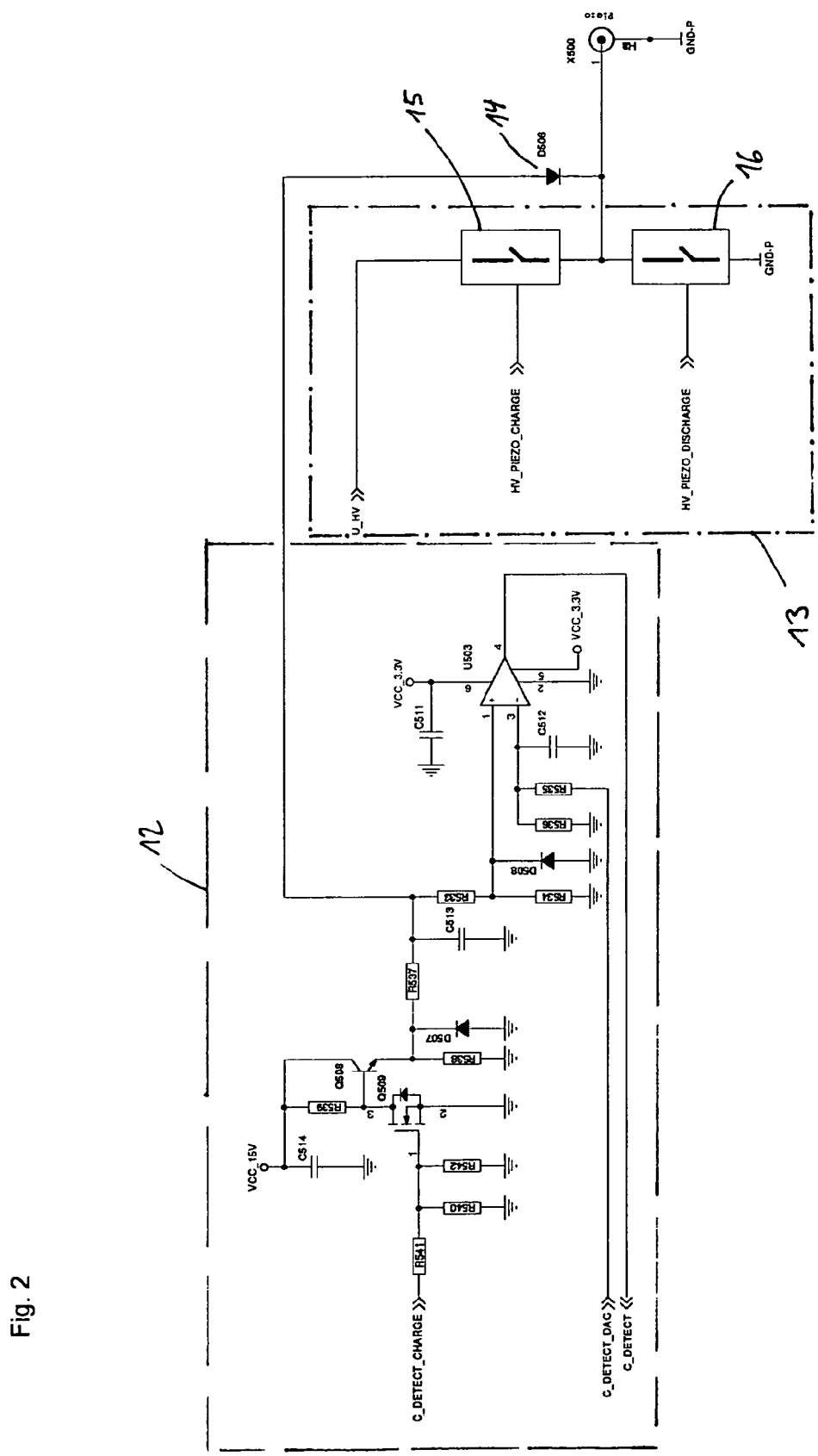
FIG. 2 shows a schematic plugging diagram of parts of the control device and the measurement device of the actuator apparatus of FIG. 1.

FIG. 2 shows a schematic plugging diagram of the measurement device 12 and the actuation control device 13, which are both integrated into the control device 11. The dashed lines do not represent connections but do only symbolize the assignment of the respective components of the plugging diagram to the measurement device 12 or the actuation control device 13, respectively. The diode 14 protects the measurement device 12 during the actuation procedure against the high supply voltage of the piezoelectric elements. The diode 14 is a High Voltage Ultrafast Diode (D506), at hand. The high voltage input of the actuation control device 13 is shown as "U_HV" in FIG. 2.

The actuation control device 13 comprises components, which are used for the actuation of the at least one actuator element, e.g. the piezoelectric elements 3. The actuation control device 13 comprises a high voltage supply U_HV, for providing 345 V, for example, to let the piezoelectric elements 3 perform an actuation. The actuation control device 13 further comprises two switches 15 and 16. Switch 15 connects U_HV to the piezoelectric elements 3 (referred to as "piezo" or "X500" in FIG. 2), if the logical signal "HV_PIEZO_CHARGE" is set by the control device to be "1", while being set to "0" by default, to make the arrangement more safe. The switch 16 connects the piezoelectric element X500 to the ground (referred to as "GND-P" in FIG. 2), if the logical signal "HV_PIEZO_DISCHARGE" is set by the control device to be "1", which is the default setting. Preferably, a few microseconds before charging the piezo X500, the signal HV_PIEZO_DISCHARGE is set to "0", which opens the switch to allow the charging of the piezo by U_HV. In particular during the performance of the measurement of the measurement device 12, the switch 16 is closed and switch 15 is open, thus U_HV being disconnected.

The measurement device 12 automatically examines the electrical capability of the actuator apparatus or its actuator, respectively. A single measurement lasts 1 to 50, 5 to 25 or 10 to 15 microseconds, typically, e.g. 13 $\mu s$. Several measurements can be provided, to increase the reliability of the result, if needed. Thus, safety is gained by using a measurement device, for the user and, further, more safety for the applications of the actuator apparatus, in particular, an improved reproducibility of application. The measurement device 12 works, as follows.

The measurement device 12, shown in FIG. 2, performs a measurement of a capacitance quantity of the piezo upon request of the control device 11. In particular, the control device 11 automatically performs the measurement, if an actuation or a motion procedure of the at least one actuator device is requested or initiated by the control device (or the user). The piezo actuator is a piezostack connected to a cable, which both can be considered as a single simple capacity. The capacitance, and thus, the status of the piezo, can be measured by several methods, which derive a capacitance quantity allowing to draw conclusions on the capacitance.

The capacitance of a typical piezo X500, can be, for example, between 1.2 and 2.6 nF, in particular 1.9 nF, in the present embodiment, wherein the actuating device comprises four actuator elements having a capacitance of 475 pF (e.g. +/−20%) each, and the connector cable 9 having a capacitance of 115 pF. For performing the measurement of the charge status of the piezo, the piezo X500 is connected to a low voltage supply ("VCC_15V" in FIG. 2) via a resistance ("R537") and a switch ("Q508", "Q509"), which is an IGBT (insulated-gate bipolar transistor) adapted to also switch high currents of several ampere (e.g., 2 A). The capacitance quantity, in the present preferred embodiment, is the time, which is needed to charge the piezo from a starting value of the charge (substantially zero) to a reference value of the charge, which is represented by the voltage signal "C_DETECT_DAC". The reference value can be predetermined and the corresponding value can be detected and stored by the control device. Once the logical signal "C_DETECT_CHARGE" is set from "0" (default setting) to "1", the piezo, i.e. the capacity, is charged according to an exponential function (~1/(1−exp(t))). If a reference value of the charge, determined before, is reached or exceeded, the control device detects this by monitoring the output "C_DETECT" of the comparator ("U503" in FIG. 2). The event is characterized by "C_DETECT" switching to a higher voltage, substantially immediately. The control device measures the period (referred to as "dt_C_DETECT") between said event and the starting trigger time, which is determined by the moment switching "C_DETECT_CHARGE" to "1".

For performing a measurement, the following status are adjusted at the control device inputs: HV_PIEZO_DISCHARGE=ON, HV_PIEZO_CHARGE=OFF, while, however, connector U_HV being under high voltage HV, C_DETECT_CHARGE=OFF. The measurement starts, if C_DETECT_CHARGE=ON is set. Then, the period dt_C_DETECT between starting and the increasing ramp of the comparator output C_DETECT is measured. Finally, C_DETECT_CHARGE=OFF is set.

An exemplary period "dt_C_DETECT" can be between 570 ns and 1350 ns (but can also differ, e.g. by a factor between 0.1 to 10), for the present embodiment, if e.g. piezos of 1.9 nF capacitance are connected to the control device 11 and work properly. If cable 9 of the piezo is not connected to plug 10, the capacitance is 0 nF, "dt_C_DETECT" ends up with e.g. 30 ns or 320 ns (simulated value based on a capacitance of e.g. 180 pF), but said time can also differ, e.g. by a factor between 0.1 to 10. The controller knows from a table that this time corresponds to a failure, and puts out an ERROR. Most importantly, the control device 11 is prevented now from performing the actuation of the piezo by switching on "HV_PIEZO_CHARGE", which avoids that an uncovered plug 10, where probably no cable is connected, becomes dangerous for the user, who touches the plug (e.g. set to 345V), by accident. This renders the actuator apparatus more safe. Another status after the measurement results from a short-cut of the cable 9, for example, where C_DETECT remains on a low level, i.e. dt_C_DETECT becomes virtually infinite, which also leads to an ERROR, which automatically prevents the actuator apparatus from initiating an actuation.

In FIG. 3, a complete pulse sequence corresponding to a motion procedure comprises several steps, typically. In a first (optional) step 21, lasting typically between 1 and 100 µs, 40 to 80 µs or 50 to 60 µs, the control device 11 detects the maximum voltage, which is to be applied to the piezo. This is done while HV_PIEZO_CHARGE=OFF. In step 22, the measurement of the capacitance value is performed, while HV_PIEZO_CHARGE=OFF. In step 23, the setting HV_PIEZO_DISCHARGE=OFF is applied and HV_PIEZO_CHARGE=ON, which causes the actuation of the piezo. Optionally, several further steps of actuation follow. At the end of the pulse sequence, the control device detects at least one further internal voltage level of the control device, in an optional step 24.

It is now referred to FIG. 4. Prior to application of the actuator apparatus and after switching on the same, the control device preferably performs another method step, related to an initialization procedure, preferably by choice of a user. The initialization procedure serves to compensate offset quantities, e.g. the influence of the leakage current of the High-Side IGBT. Thus, the application of the apparatus becomes more reliable. In the first step 31, the offset quantity is determined by setting HV_PIEZO_DISCHARGE=ON, HV_PIEZO_CHARGE=OFF, C_DETECT_CHARGE=OFF, C_DETECT_DAC, the voltage ramp is driven from 0 to the event when C_DETECT jumps to 0. The corresponding value of C_DETECT_DAC is saved by the control device as value X1. Step 31 is finished.

In Step 32, the maximum charge voltage of the piezo is detected, which can be used to set the reference value for the measurement of the capacitance quantity. In step 24, the settings are HV_PIEZO_DISCHARGE=ON, HV_PIEZO_CHARGE=OFF, C_DETECT_CHARGE=ON, initially, followed by a delay of e.g. $\Delta t\_1=10$ ms, which charges the piezo; then: stepwise or continuously reducing the voltage ramp C_DETECT_DAC starting from the maximum charge voltage, until C_DETECT jumps to 1, detecting the value of the ramp which corresponds to said event and storing the corresponding C_DETECT_DAC as the value X2 in the control device.

In step 33, the reference value is determined according to ((X2−X1)*0.85)+X1, and is stored and set for the subsequent operation of the actuator apparatus. This reference value corresponds to 85% of the capacitor charge voltage considering the actual offset quantities as well as allowances of the supply voltage. Instead of the preferred value 85% (Xf=0.85), also another fraction value Xf can be used.

Preferably, generally another additional procedure can be provided to improve the precision of the measurement of the electrical capacitance quantity. A calibration of parasitic capacitances accounts for parasitic capacitances of the measurement device itself or, respectively, compensates the parasitic capacitances caused by the circuit board, which carries the IGBT's, the diodes etc. of the measurement device. Said calibration procedure provides a standard measurement of the capacitance quantity, while the actuator elements or the actuating device respectively, is not connected to the measurement device, or the control device, respectively. Said calibration procedure is performed e.g. after the initialization procedure, which determines an offset quantity and detects a parasitic capacitance quantity, which can be a time dt_C_DETECT, which, preferably, is stored permanently as a value dt_C_DETECT_PARA by memory means of the measurement device or, respectively the control device. Said memory means can be an EEPROM, which can be provided on the same circuit board. During standard operation of the actuator apparatus, which applies the measurement of the capacitance quantity, the value dt_C_DETECT_PARA is used to determine the corrected capacitance quantity dt_C_DETECT_CORRECTED, e.g. by dt_C_DETECT_CORRECTED=dt_C_DETECT−dt_C_DETECT_PARA, referring in particular to the embodiment described before.

The invention claimed is:
1. An actuator apparatus for generating a linear piercing and/or cutting motion of a tool, said tool comprising a capillary or a microdissector needle for piercing and/or dissection of cell membranes or chromosomes, the actuator apparatus comprising:
- at least one electrically controlled actuator element, wherein said element is a piezoelectric element,
- a motion section, at which the capillary or the microdissector needle can be arranged lengthwise along a linear direction and which is linked to the at least one actuator element,
- an electrical control device for controlling the at least one actuator element, the electrical control device comprising electric circuits,
- an electrical measurement device, which is configured to perform a measuring method for measuring at least one electrical capacitance quantity of the at least one actuator element,
- wherein the electrical capacitance quantity is used to provide information on the capability status of the actuator apparatus,
- wherein the actuator apparatus provides connector means which serve to connect the at least one actuator element to the control device, in particular, for applying an output voltage to the at least one actuator element, and
- wherein the control device provides means for controlling the output voltage, which is put out by said connector means and that the control device is configured to apply a first output voltage, which is used to perform the measurement of the capacitance quantity, and to temporarily provide a second output voltage, which is used to let the at least one actuator element perform an actuation, causing the linear piercing and/or cutting motion of the capillary or the microdissector needle, the linear piercing and/or cutting motion comprising a number of forward and backward motions along the linear direction having an amplitude of between 0.01 µm and 1.8 µm,
- wherein said measuring method for measuring at least one electrical capacitance quantity of the at least one actuator element is configured to:
  - detect failures of the at least one actuator element or the connector means or the electric circuits,
  - detect the presence or absence of the at least one actuator element being connected or not connected to the electric measurement device, or
  - detect a type or configuration of the at least one actuator element being connected to the electric measurement device.

2. The actuator apparatus according to claim 1 characterized in that the control device provides means for controlling the actuation of the at least one actuator element according to a motion procedure and that the control device provides means for automatically initiating the performance of said measuring method upon initiation of said actuation.

3. The actuator apparatus according to claim 2 characterized in that the motion procedure is a predetermined motion procedure or a user controlled motion procedure.

4. The actuator apparatus according to claim 1 characterized in that a first status and a second status of the actuator apparatus are provided and that the control device provides means for changing the actuator apparatus from the first status to the second status in dependence on the result of said measuring.

5. The actuator apparatus according to claim 4 characterized in that the second status is defined such that the actuator apparatus consumes less energy in the second status than in the first status.

6. The actuator apparatus according to claim 4 characterized in that the second status is defined such that the actuator apparatus uses a modified control method for controlling the actuation of the at least one actuator element in the second status compared to the first status.

7. The actuator apparatus according to claim 6 characterized in that said control method uses a modified output voltage for controlling the actuation of the at least one actuator element in the second status compared to the first status.

8. The actuator apparatus according to claim 1 characterized in that the electrical capacitance quantity is a time period.

9. The actuator apparatus according to claim 1 characterized in that the measurement device comprises means to measure the charge of the at least one actuator element and that the measurement device comprises a comparator circuit which compares the charge of the at least one actuator element with a reference value.

10. The actuator apparatus according to claim 1 characterized in that the measurement device comprises a time measuring device for measuring time periods between electrical signals with a precision of at least 1 ns, 10 ns or 100 ns.

11. The actuator apparatus according to claim 1 characterized in that the measurement device comprises means to measure the charge of the at least one actuator element and means to measure the time period, which is needed for the at least one actuator element to charge from a starting value of the charge to a reference value of the charge of the at least one actuator element.

12. A method for determining the capability status of an actuator apparatus for generating a linear piercing and/or cutting motion of a tool, wherein said tool comprises a needle, a capillary or a microdissector needle for piercing and/or dissection of cell membranes or chromosomes, the actuator apparatus comprising:
- at least one electrically controlled actuator element, wherein said element is a piezoelectric element,
- a motion section, at which the needle, the capillary or the microdissector needle can be arranged lengthwise along a linear direction and which is linked to the at least one actuator element, which is a piezoelectric element,
- an electrical control device for controlling the at least one actuator element, the electrical control device comprising electric circuits,
- an electrical measurement device, which is configured to perform a measuring method for measuring at least one electrical capacitance quantity of the at least one actuator element,
- wherein the electrical capacitance quantity is used to provide information on the capability status of the actuator apparatus,
- wherein the actuator apparatus provides connector means which serve to connect the at least one actuator element to the control device, in particular, for applying an output voltage to the at least one actuator element, and
- wherein the control device provides means for controlling the output voltage, which is put out by said connector means and that the control device is configured to apply a first output voltage, which is used to perform the measurement of the capacitance quantity, and to temporarily provide a second output voltage, which is used to let the at least one actuator element perform an actuation, causing the linear piercing and/or cutting motion of the needle, the capillary or the microdissector needle, the linear piercing and/or cutting motion comprising a number of forward and backward motions along the linear direction having an amplitude of between 0.01 µm and 1.8 µm, the method comprising the steps:
  measuring at least one electrical capacitance quantity of the at least one actuator element of the actuator apparatus using the electric measurement device of the actuator apparatus;
  using the measured capacitance quantity to determine the capability status of the actuator apparatus, wherein said measuring of at least one electrical capacitance quantity of the at least one actuator element is configured to:
    detect failures of the at least one actuator element or the connector means or the electric circuits;
    detect the presence or absence of the at least one actuator element being connected or not connected to the measurement device, or
    detect a type or configuration of the at least one actuator element being connected to the measurement device.

* * * * *